US005144671A

United States Patent [19]

Mazor et al.

[11] Patent Number: 5,144,671

[45] Date of Patent: Sep. 1, 1992

[54] METHOD FOR REDUCING THE SEARCH COMPLEXITY IN ANALYSIS-BY-SYNTHESIS CODING

[75] Inventors: Baruch Mazor, Newton Centre; Dale E. Veeneman, Southborough, both of Mass.

[73] Assignee: GTE Laboratories Incorporated, Waltham, Mass.

[21] Appl. No.: 494,071

[22] Filed: Mar. 15, 1990

[51] Int. Cl.[5] .......................... G10L 5/00; A61F 15/38

[52] U.S. Cl. ...................................... 381/36; 364/419; 381/47

[58] Field of Search ...................... 381/36, 47; 364/419

[56] References Cited

PUBLICATIONS

Atal et al, "Stochastic Coding of Speech at Very Low Bit Rates" Proc. IEEE Int. Conf. Comm., pp. 1610-1613 (Apr. 1984).

Trancoso et al, "Efficient procedures for finding the optimum innovation in stochastic coders," Proc. IEEE Int. Conf. Acoust., Speech, Signal Processing, pp. 2375-2378 (Apr. 1986).

Anderson, "Tree Coding of Speech," IEEE Trans. Inform. Theory, vol. IT-21, pp. 379-387 (Jul. 1975).

Lin, "Speech coding using efficient pseudo-stochastic block codes," Proc. IEEE Int. Conf. Acoust., Speech, Signal Processing, pp. 1354-1357 (Apr. 1987).

*Primary Examiner*—Emanuel S. Kemeny

*Attorney, Agent, or Firm*—Victor F. Lohmann, III

[57] ABSTRACT

A method of encoding speech includes a limited search of a tree-code excitation codebook with a closed loop gain calculation for each test path under consideration. The gain calculation occurs when minimizing an error distance measurement between a synthetic signal defined by each test path being considered and the appropriate speech signal by optimizing a scaling factor of the synthetic signal. The encoding method achieves a significant reduction in computational complexity with minimal loss of performance.

9 Claims, 3 Drawing Sheets

METHOD FOR REDUCING THE SEARCH COMPLEXITY IN ANALYSIS-BY-SYNTHESIS CODING

FIELD OF THE INVENTION

The present invention relates to the field of speech coding and, in particular, a method of encoding a speech signal employing a tree-structured code, a closed-loop gain calculation, and a limited search procedure.

BACKGROUND OF THE INVENTION

Analysis-by-synthesis speech coders operate by determining coding parameters at the encoder which minimize a distortion measure between the coded (synthetic) speech and the original speech. These parameters are then forwarded to the decoder where the coded speech is reconstructed. In a conventional system using the above encoding scheme, the encoder searches a "colored" codebook created from an appropriately filtered "white" codebook to find a codeword which will represent a given input frame of speech with minimum error. The index of this codeword is then passed to the receiver where it is used to synthesize the output speech. Known as stochastic coding, this technique is discussed by Atal and Schroeder in "Stochastic Coding of Speech at Very Low Bit Rates", Proc. IEEE Int. Conf. Comm., pp. 1610-1613 (April 1984), and is illustrated in block diagram format in FIG. 1.

As shown, the first sequence of random (e.g., Gaussian) samples represented by the vector y is drawn from a codebook, scaled by a gain factor G, and filtered by A(z) to produce the synthetic speech vector . The synthetic speech is then compared with the input speech vector s to calculate the distance E between them. This distance measure is typically the mean weighted squared error. This iterative procedure of coloring and distance calculation is repeated for every entry in the codebook until the Mth codeword has been processed. The index of the codeword that gives the smallest E for the current speech frame being encoded is forwarded to the receiver so that analysis can begin with the next frame. Additionally, the filter and gain parameters are updated periodically and transmitted to the receiver.

The codebook illustrated in FIG. 1 is known as a block code in which each entry is represented in its entirety as a separate sequence of samples. This is the basic and most common form of codebook used in analysis-by-synthesis coders. Although it is considered the most optimal codebook, a great deal of computation is required to search it. Using the operation of a multiply-and-add as a figure of complexity, a coder with a codebook of M codewords, frame length (dimension) of N, and a coloring filter of order P requires on the order of $M \cdot N \cdot P$ operations to color the codebook. In addition, about $M \cdot N \cdot 2$ operations are needed to calculate the M distances, resulting in a total search complexity figure of $M \cdot N \cdot (P+2)$. For example, a coder with $M=1024$, $N=40$, and $P=10$ requires about 491,520 operations to search the codebook for each frame.

Originally, analysis-by-synthesis coders determined the gain once for each frame, usually to match the energy of the synthetic speech to that of the input. This type of procedure, discussed in Atal and Schroeder, supra, is referred to as open-loop because the gain is determined prior to and without regard to the codeword selection. A more effective procedure in which the gain is calculated in a closed-loop is discussed by Trancoso and Atal in "Efficient procedures for finding the optimum innovation in stochastic coders," Proc. IEEE Int. Conf. Acoust., Speech, Signal Processing, pp. 2375-2378, (Apr. 1986). In this approach, the optimum gain for each codeword is calculated so as to minimize the error distance between the synthetic speech computed from that codeword and the input speech. The codeword/gain pair that yields the smallest error for that frame is then used. Because the optimum gain may be determined as part of the distance calculation, there is no real increase in complexity, while a significant increase in performance results.

Recognizing that much of the computational complexity is due to the search of the codebook, other recent efforts have focused on this complexity by using codebooks with some dependencies among codewords. One such codebook is a tree-structured code discussed by Anderson in "Tree Coding of Speech," IEEE Trans. Inform. Theory, vol. IT-21, pp. 379-387(July 1975). In general, a tree-code grows from a root node and has q branches stemming from each node and n codeletters (samples) per branch. A tree of depth L will contain $M=q^L$codewords, each of frame length $N=n \cdot L$, with a q-level path map sequence through the tree corresponding to a unique sequence of codeletters (a single codeword) that is used as the encoder's index in the transmission. Due to the interdependency between codewords, a tree-structured codebook provides reduction in the complexity of the coloring and distance calculation at the cost of some increase in distortion. The computational complexity of a tree code with M codewords, dimension N, order P filter, and a branching factor q is approximated as $[(q/q-1)(M-1)](N/\log_q M)(P+2)$, where $\log_q M$ is the depth of the tree, $[q/(q-1)](M-1)$ is the total number of branches in the tree, and $N/\log_q M$ is the number of letters per branch. A binary tree ($q=2$) applied to the same example as before with $M=1024$, $N=40$, and $P=10$ requires about 98,208 operations to search the codebook for each frame, about one-fifth the complexity of the block code.

A further reduction in the computational complexity may be realized by not searching the entire tree as in an exhaustive search, but rather performing a limited search. One such limited search procedure is the M-algorithm disclosed by Anderson, supra. The algorithm visits at each stage of the tree a fixed number $q \cdot M_s$ of branches extending out from $M_s$saved paths which lead up to the present stage. Only the best $M_s$ (those with lowest distance) paths are saved from these visited paths for searching in the next stage. At the final stage of the tree, the codeword associated with the best path is selected.

The search intensity is commonly measured by the number of survivors $M_s$ saved at each stage. Since the coder employing such a limited search visits a finite number ($q \cdot M_s$ at most) of branches at each stage of the tree, there is consequently a significant reduction in computational complexity compared to the exhaustive tree search. The computational complexity figure for this limited search procedure is approximated by the product of the branching factor, the number of survivors, the number of letters per branch, the depth, and $(P+2)$, and is expressed mathematically as $qM_snL(P+2)=qM_sN(P+2)$. Using the binary tree ($q=2$) example above with the M-algorithm search procedure (and adjusting the complexity figures to allow for the growth of the tree), the approximate number of operations for different search intensities are: 960 for $M_s=1$, 1824 for $M_s=2$, 3360 for $M_s=4$, and 6048 for $M_s=8$. This clearly represents a reduction in the computational complexity, but at the cost of a sub-optimal solution since a potential lowest error path through the entire tree may be discarded at an early stage.

Disadvantageously, conventional coders using a tree-structured code (either exhaustively searched or using a limited search) have always used open-loop gain calculation. However, Lin in "Speech coding using efficient pseudo-stochastic block codes," Proc. IEEE Int. Conf. Acoust., Speech, Signal Processing, pp. 1354–1357 (Apr. 1987) reported a coder with a tree-structured code using the more effective closed-loop gain calculation, but also required an exhaustive search of the tree.

OBJECTS OF THE PRESENT INVENTION

It is a primary object of the present invention to obviate the above-noted and other disadvantages of the prior art.

It is a further object of the present invention to provide an encoding scheme which employs a tree-structured code, a closed-loop gain calculation, and a limited search procedure.

It is a further object of the present invention to provide a method of speech encoding characterized by a significantly lower computational complexity as compared to that of a block code or of any exhaustively searched tree code.

It is a further object of the present invention to provide an encoding scheme where the optimal calculation of a closed-loop scaling factor allows a limited search procedure in a tree-code to achieve minimal loss in performance compared to that of exhaustive searches.

SUMMARY OF THE INVENTION

The present invention is directed to a method of encoding a frame of input speech signal by performing a limited search of a tree-code excitation codebook to find a codeword achieving an optimal representation of the speech frame. The frame is partitioned into a predetermined number of sample segments of length equal to the length of each branch in a respective stage of the tree-code. Each branch of the tree-code represents a sequence of codeletters so that each full path through the tree-code represents a codeword.

At each stage of the tree-code, the limited searching involves identifying a set of test paths by extending out a predetermined number of branches from a limited number of saved paths which lead up to the current stage from a root node. The respective codeletters of these extended branches are then colored with a coloring filter. The encoding method next minimizes an error distance measurement between a synthetic signal defined by each test path and the sequence of sample segments up to the current stage by optimizing a scaling factor of the synthetic signal. A limited number of these test paths are saved based on lowest relative distance measurements. These surviving test paths serve as the saved paths from which further searching occurs in a next stage.

The steps of path identification, codeletter coloring, error distance minimization by optimal scaling, and path saving are repeated in each successive stage of the tree-code. After the final stage has been searched, the single one of the saved full paths having the lowest relative distance measurement represents the codeword achieving optimal representation of the frame of input speech signal.

DETAILED DESCRIPTION OF PREFERRED EMBODIMENTS

Figure 1:
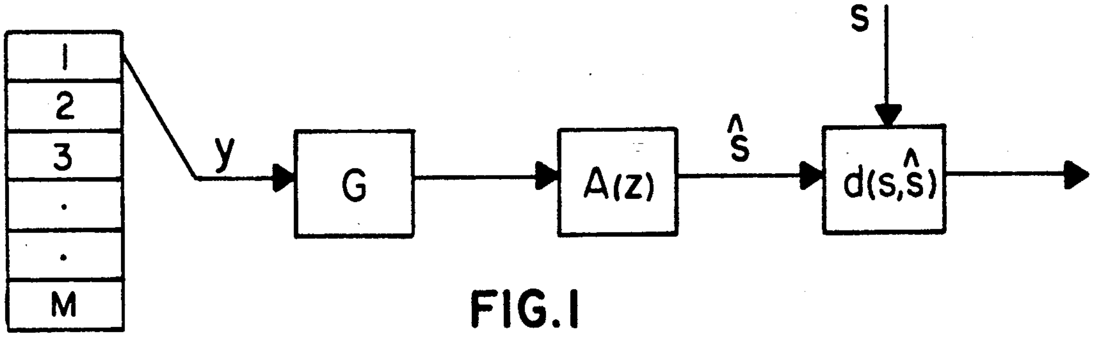
FIG. 1 is a block diagram of a stochastic encoder used in conventional speech coding systems.

The novel encoding technique of the present invention employs a limited-search of a tree-structured code and an optimal closed-loop gain calculation for each of the paths pursued by the limited searching. The encoding method performs at each stage of the tree-code an iterative search procedure which pursues a finite number of paths and saves a limited number of them as surviving paths from which further searching occurs in the next stage. At this next stage, a predetermined number (at most $q \cdot M_s$) of branches are extended out of these $M_s$ saved paths to create a new set of test paths to be pursued. The respective codeletters of the extended branches are colored with a coloring filter, and a minimized error distance measurement is calculated between a synthetic signal defined by each test path being considered and the input signal up to the current stage of the tree. The minimization occurs by optimizing a scaling factor of the synthetic signal. A limited number of paths having the lowest relative distance measurements are saved for the next successive stage.

A novel feature of the present invention is that instead of using an independently determined (open-loop) gain to scale these colored test paths, an optimum gain is calculated for each test path. This gain is optimally calculated so that the error distance measurement for each test path is minimized. The optimal gain of a particular test path is considered to be cumulative because it is calculated for the entire length of the path up to the current stage and not for a portion of the path. At each stage, therefore, a cumulatively optimum gain and a corresponding error distance are found for each test path. As noted above, only those limited number of paths from the set of test paths which have the lowest relative error distance measurement are saved for the search procedure in the next stage. At the final stage of the tree, the codeword associated with the best path is selected as the optimal representation of the frame of input speech signal.

The encoding method according to the present invention is discussed below with reference to the exemplary tree-code of FIG. 2. This tree-code excitation codebook has a depth $L=4$with $q=2$ branches extending from each node and $n=3$ codeletters per branch. The tree contains $M=q^L=16$ codewords, each of frame length $N=n \cdot L=12$ codeletters. At each stage of the tree, only $M_s=2$ paths are saved before searching begins in the next stage by extending out at most $q \cdot M_s=4$ branches from these $M_s$saved paths. Although the tree-code is characterized with these parameters to facilitate an understanding of the limited search procedure used in the present invention, the tree-code is shown for illustrative purposes only and should not serve as a limitation of the present invention since the novel encoding method disclosed herein is useful with any tree-structured code.

The frame of input speech signal to be encoded is denoted by the vector s and is partitioned as shown into the four segments located above the tree wherein each segment consists of three speech samples. In general, the length of each segment is equivalent to the length of each of the branches in a respectively corresponding stage of the tree. For example, the segment denoted by $s_4s_5s_6$ is associated with stage 2, where $y_4y_5y_6$ is the codeletter sequence of a particular branch in that stage. Although the branches are of uniform length throughout the exemplary tree-code, other tree-codes with a variable number of codeletters per branch among the stages are included within the scope of this invention.

Figure 2:
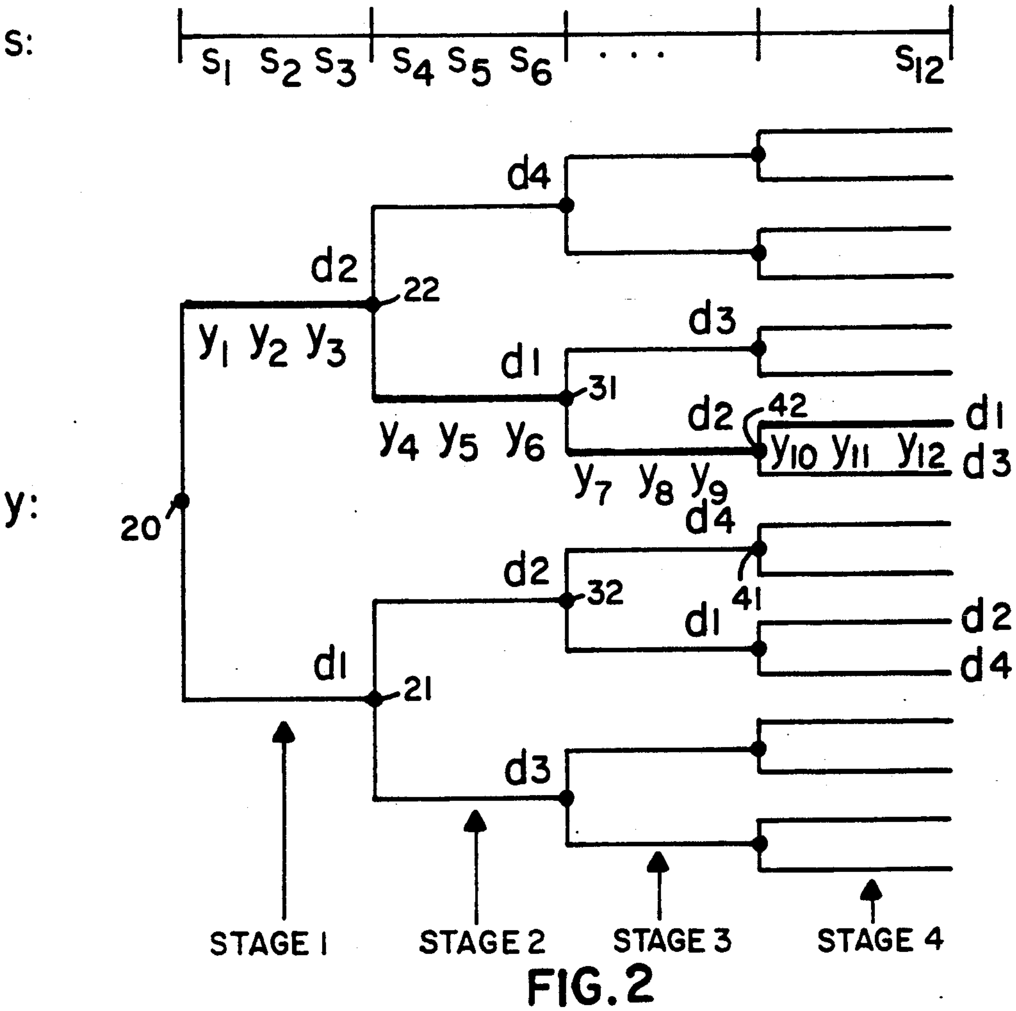
FIG. 2 is a diagram of an exemplary tree-code for illustrating the limited search procedure employed by the encoding method of the present invention.

The encoding method begins in the tree-code of FIG. 2 by extending out two branches from root node 20 in order to identify the test paths to be pursued in stage 1. Although up to four branches may be extended out, the geometry of the tree limits the searching to only two branches in stage 1. The error distance measurement for each of the extended branches following coloring of the respective codeletters is represented by the distance designations $d_1$ and $d_2$.

In general, each $d_i$ is the cumulative distance between s, the speech segments up to the present stage, and , the synthetic signal representing the filtered and scaled code-letter sequence corresponding to the particular test path. The error distance measurement is minimized by optimizing a scaling (gain) factor of the synthetic signal. Thus, a new gain is calculated along with each cumulative distance so that even if two paths share common earlier branches, the samples of each associated with those branches may be different because of different gains for the paths.

For the purposes of this exemplary tree-code, the inequality $d_1<d_2<d_3<d_4$ expresses the relationship among four distance measurements used in the tree-code. Thus, FIG. 2 indicates that the distance measurement for the upper branch in stage 1 with codeletter sequence $y_1y_2y_3$ is less than that for the lower branch.

In stage 2, two branches are extended out of each of nodes 21 and 22 so that four test paths are now being considered. Each test path consists of one of the two saved branches from stage 1 linked with a respective one of the four extended branches. An error distance measurement is calculated for each of the test paths, and the results are indicated by an appropriate distance ranking $d_{i=1\ to\ 4}$ on each branch. Again, the distance measurements are minimized by optimizing a scaling factor of each synthetic signal so that each test path has a new cumulative gain associated with it.

The $d_1$ measurement, for example, represents the error distance calculation between s, the input sample sequence $s_1s_2s_3s_4s_5s_6$, and , the synthetic signal derived from the codeletter sequence $y_1y_2y_3y_4y_5y_6$. Since only two test paths survive the search at each stage, the test paths associated with the branches in stage 2 marked by measurement designations $d_1$ and $d_2$ are saved for the next stage 3, whereby branch extension in stage 3 occurs from nodes 31 and 32.

The test paths in stage 3 are identified by extending out two branches from each of nodes 31 and 32. After the code-letter sequences of these branches are colored and a minimized error distance measurement is calculated for each test path by optimizing a scaling factor of the synthetic signal, the test paths having the $d_1$ and $d_2$ error distance measurements are saved. As in each of the preceding stages, the $d_i$ for each test path is the cumulative distance between the input speech signal (s vector) up to the present stage and the synthetic signal for the respective test path.

In the last stage, two branches are extended out from each of nodes 41 and 42 which belong to the two saved paths linked to root node 20 that survived the searching in the first three stages. The path associated with the branch designated by $d_1$ has the lowest error distance measurement of the two saved paths traversing the entire tree-code. Thus, the codeword represented by the codeletter sequence $y_{i=1\ to\ 12}$corresponding to the indicated path is the optimal representation of the input speech frame $s_{i=1\ to\ 12}$resulting from the particular limited search procedure utilized in this exemplary tree-code. Paired with this optimal codeletter sequence is a final, cumulatively optimum gain which is calculated during minimization of the $d_1$ measurement.

An exemplary coder was constructed using 1024 codewords (Gaussian distributed samples), a frame length of 40, a cascaded coloring filter (10th order linear predictive [LP] formant filter and 3rd order pitch filter), and a mean weighted squared error measure. A long sample of speech was encoded using this coder with the 1024 codewords arranged into the following structures: a block code, three tree-codes with constant branching factors (q) of 32, 4, and 2, a tree-code with a variable branching factor of 16,4,4,4 for the four stages, and overlapped codes (from 1 to 5 samples shift). The trees were tested using a limited search ($M_s=1$ to 8) procedure and a closed-loop gain calculation in accordance with the present invention. For comparison purposes, an exhaustive search of the tree was also performed. The partial results of these encoding tests are presented in FIG. 3, where the segmental SNR (averaged signal to noise ratio in dB of 20 msec segments) is plotted against the computational complexity figure for a single frame.

The complexity axis is plotted as the base 2 logarithm of the operations so that each marking is a numerical measure of complexity which represents twice the number of operations as that associated with the previous marking. Curve 31 represents the performance envelope of the tested tree codes and indicates the variation of segmental SNR as a function of complexity when the number $M_s$ of saved paths used in the limited search procedure is increased. In particular, the single-survivor ($M_s=1$) binary tree marks the beginning of the curve, and the exhaustively-searched 16,4,4,4 tree is the final data point on the upper plateau of the curve. Curve 32 represents the performance of the overlapped and the block codes.

Figure 3:
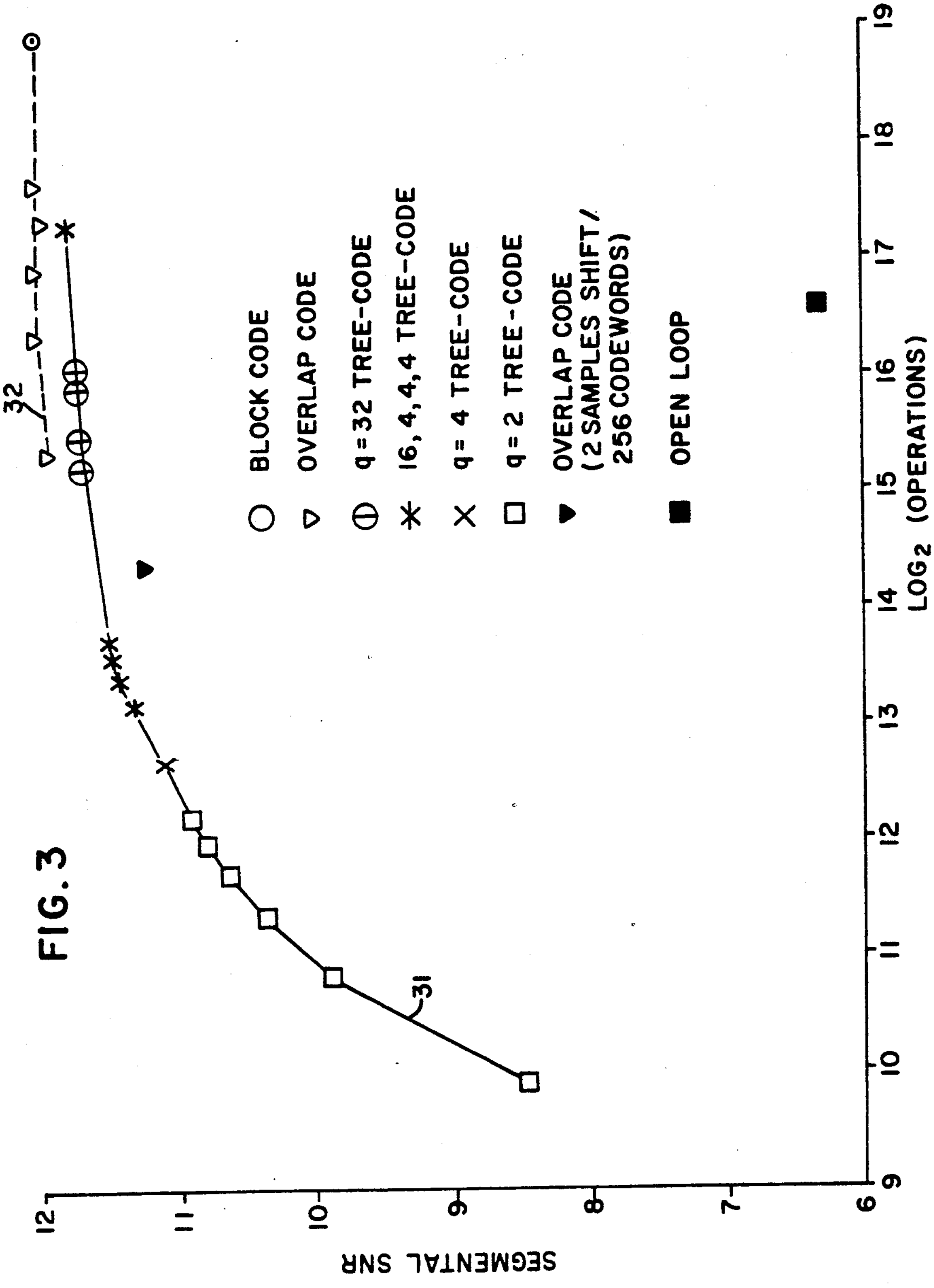
FIG. 3 graphically compares the performance results of an encoder constructed in accordance with the present invention and conventional coders using various combinations of code structures and search procedures.

The significance of FIG. 3 is illustrated by making an exemplary comparison between the performance of the block code and a tree-code with a complexity of between 13 and 14. As indicated, the number of operations for the tree-code is lower by a factor of approximately 50 relative to the block code. Advantageously, the corresponding 0.67 dB difference in SNR causes a negligible perceived loss in speech quality. The complexity reduction is also significant over the overlapped codes (a factor of nearly 10 for a shift of 2). The complexity is even lower (about one-half) than that of a 2 sample overlapped code with only 256 codewords, which in this case has inferior performance. Also shown is the decidedly poor performance of the coder using the open-loop gain calculation for an exhaustively searched binary tree.

Figure 4:
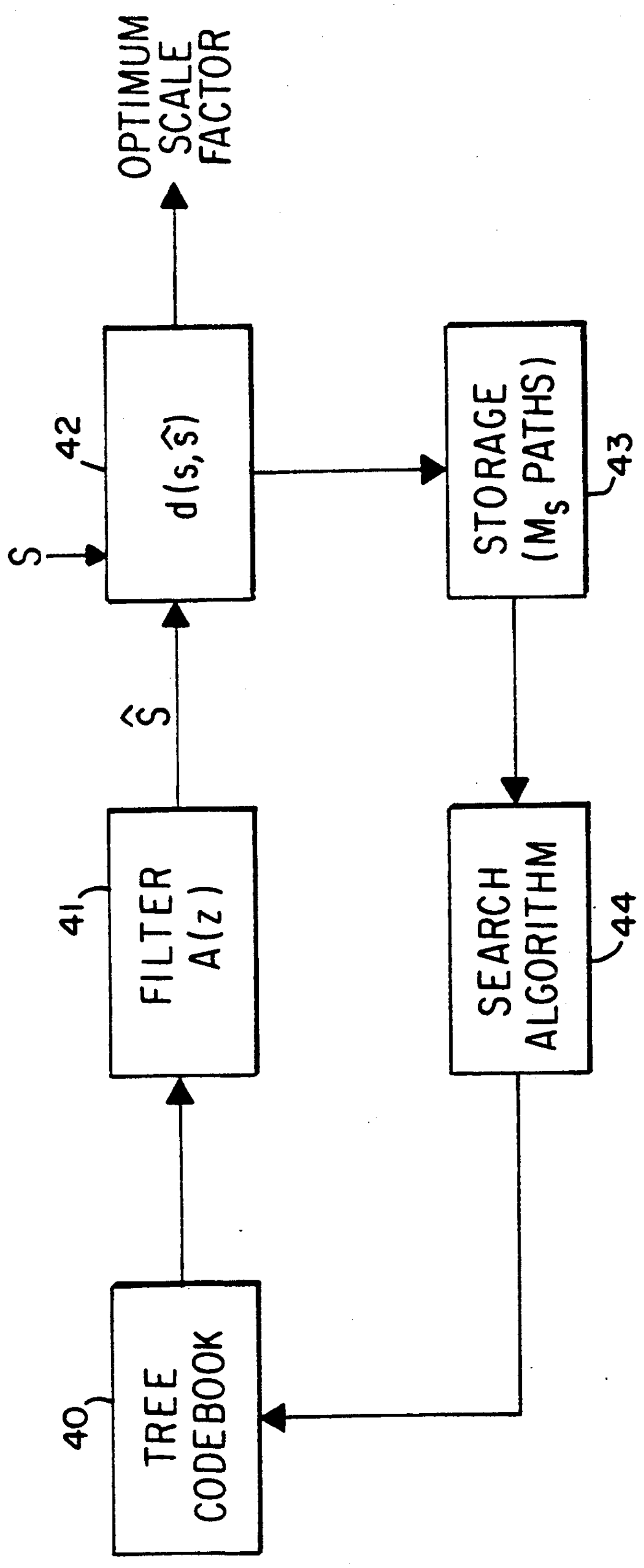
FIG. 4 shows a block diagram of a system for implementing the encoding method of the present invention.

FIG. 4 is a block diagram showing the components of a system for implementing the encoding method described hereinabove. A tree code book 40 includes the code letter sequences from which a code word is selected according to the encoding method. A coloring filter 41 with a transfer function A(z) filters the respective code letters of the descending branches extending from the saved paths as identified by the search algorithm 44. The synthetic signal s corresponding to the code letter sequences of each of the tree paths under consideration is applied to subsystem 42 where an error distance measurement d(s,s) is computed between the synthetic signal and a speech sample s. This minimization involves the optimization of a scaling factor of the synthetic signal s. The $M_s$ number of paths having the lowest relative error measurements are stored in storage means 43. The $M_s$ stored paths, and their respective code letter sequences, are used by the search algorithm 44 in advancing to the next stage of the tree to generate a next set of code letter sequences.

What has been shown and described herein is a method to reduce the search complexity in "analysis-by-synthesis" coders with minimal loss of performance. The novelty of the encoding method of the present invention is directed to the use of a closed-loop gain calculation in a limited search of a tree-structured code. The achievable reduction in computational complexity is very important, as it makes economical implementations of this type of coder feasible without sacrificing quality. Furthermore, the present invention offers flexibility by allowing the gradual modification of coder complexity over a very broad range.

What is claimed is:

1. A method of encoding a frame of input speech signal using a tree-code excitation codebook wherein each branch of said tree-code represents a sequence of codeletters and each full path through said tree-code represents a codeword, comprising the steps of:

partitioning the speech frame into a predetermined number of sample segments of length equal to the length of each branch in a respective stage of said tree-code;

performing a limited search of said tree-code to find a codeword achieving an optimal representation of said input speech signal, said search operating so that at each stage of said tree-code only a limited number of paths are saved from which further searching occurs:

said limited search including at each current stage of said tree-code the steps of identifying the paths to be currently searched by extending out a predetermined number of branches from the saved paths which lead up to the current stage from a root node, filtering the respective codeletters of said extended branches with a coloring filter, minimizing an error distance measurement between a synthetic signal defined by each path being currently searched and the sequence of sample segments up to the current stage by optimizing a scaling factor of said synthetic signal, and saving those limited number of paths having the lowest distance measurements relative to the measurements of the other currently searched paths;

whereby the limited searching continues into the next stage by repeating the steps of path identification, codeletter filtering, error distance minimization by optimal scaling, and path saving so that after reaching the last stage of said tree-code, the single one of the saved full paths having the lowest relative distance measurement represents the code-word achieving an optimal representation of said frame of input speech signal.

2. The encoding method as recited in claim 1 wherein said coloring filter is periodically adaptive.

3. A method of encoding a frame of input speech signal using a tree-code excitation codebook wherein each branch of said tree-code represents a sequence of codeletters and each full path of said tree-code represents a codeword, comprising the steps of:

partitioning the speech frame into a predetermined number of sample segments of length equal to the length of each branch in a respective stage of said tree-code;

at a current stage of said tree-code, the steps of identifying a set of test paths by extending out a predetermined number of branches from a limited number of saved paths which lead up to said current stage from a root node, filtering the respective codeletters of said extended branches with a coloring filter, minimizing an error distance measurement between a synthetic signal defined by each test path and the sequence of sample segments up to the current stage by optimizing a scaling factor of said synthetic signal, and saving those limited number of paths from said set of test paths on the basis of lowest relative distance measurements; and repeating in each subsequent stage the steps of path identification, codeletter filtering, error distance minimization by optimal scaling, and path saving so that after reaching the last stage of said tree-code, the single one of the saved full paths having the lowest relative distance measurement represents a codeword achieving an optimal representation of said frame of input speech signal.

4. The encoding method as recited in claim 3 wherein said coloring filter is periodically adaptive.

5. A method of encoding a frame of input speech by performing a limited search of a tree-code, said search using a tree-code excitation codebook wherein each branch of said tree-code represents a sequence of codeletters and each full path through said tree-code represents a codeword, and wherein said speech frame is partitioned into a predetermined number of sample segments of length equal to the length of each branch in a respective stage of said tree-code, comprising at each successive stage of said tree-code the steps of:

identifying a set of current test paths by extending out a predetermined number of branches from a limited number of saved paths which lead up to the current stage from a root node of said tree-code;

filtering the respective codeletters of said extended branches with a coloring filter;

minimizing an error distance measurement between a synthetic signal defined by each current test path and the sequence of sample segments up to the current stage by optimizing a scaling factor of said synthetic signal; and saving those limited number of test paths having the lowest distance measurements relative to the measurements of the other current test paths;

whereby the single one of the saved full paths having the lowest distance measurement represents a codeword achieving an optimal representation of said frame of input speech signal.

6. The encoding method as recited in claim 5 wherein said coloring filter is periodically adaptive.

7. A method of encoding a frame of input speech signal using a tree-code excitation codebook having a plurality of nodes arranged in cascaded stages and interconnected by branches, wherein each branch represents a sequence of code-letters and a node sequence through all of said stages represents a codeword, comprising the steps of:

partitioning the speech frame into a predetermined number of sample segments of length equal to the length of each branch in a respective stage of said tree-code;

at a current stage of said tree-code, the steps of visiting a predetermined number of branches each extending out from a node belonging to a saved node sequence linked to a root node, wherein each branch extension creates a respective nodal test link, filtering the respective codeletters of said extended branches with a coloring filter, minimizing an error distance measurement between a synthetic signal defined by each nodal test link and the sequence of sample segments up to the current stage by optimizing a scaling factor of said synthetic signal, and saving those limited number of node sequences which correspond to the nodal test links having the lowest relative distance measurements; and repeating in each subsequent stage the steps of branch visiting, codeletter filtering, error distance minimization by optimal scaling, and node sequence saving so that after reaching the last stage of said tree-code, the single one of the saved node sequences having the lowest relative distance measurement represents a codeword achieving an optimal representation of said frame of input speech signal.

8. The encoding method as recited in claim 7 wherein said coloring filter is periodically adaptive.

9. A method of encoding a speech signal, comprising the steps of:

constructing a multi-stage tree-codebook having a plurality of nodes, wherein each node has a desired number of descending branches each extending to a respective succeeding node;

each of said branches having a respective number of codeletters assigned to said branch, wherein a sequence of codeletters is represented in said tree by a connection of nodes defining a respective path;

generating at a current stage of said tree a set of codewords each defined by a sequence of codeletters represented in the tree as a saved path leading up to said current stage and extended out to a next stage by a one of the respective descending branches;

filtering the respective codeletters of said extended descending branches;

minimizing an error distance measurement between a speech sample and a synthetic signal corresponding to each of said generated codewords by optimizing a scaling factor of said synthetic signal;

storing a limited number of said generated codewords based on lowest relative error distance measurement, wherein a tree path corresponding to each stored codeword serves as a saved path as said generating step advances to a next stage in said tree-codebook.

* * * * *